US009321707B2

(12) United States Patent
Tirtowidjojo et al.

(10) Patent No.: US 9,321,707 B2
(45) Date of Patent: Apr. 26, 2016

(54) PROCESS FOR THE PRODUCTION OF CHLORINATED PROPENES (71) Applicant: BLUE CUBE IP LLC, Midland, MI (US)

(72) Inventors: Max M. Tirtowidjojo, Lake Jackson, TX (US); John D. Myers, Baton Rouge, LA (US)

(73) Assignee: Blue Cube IP LLC, Midland, MI (US)

( * ) Notice: Subject to any disclaimer, the term of this patent is extended or adjusted under 35 U.S.C. 154(b) by 0 days.

(21) Appl. No.: 14/429,248

(22) PCT Filed: Sep. 13, 2013

(86) PCT No.: PCT/US2013/059603
§ 371 (c)(1),
(2) Date: Mar. 18, 2015

(87) PCT Pub. No.: WO2014/046970
PCT Pub. Date: Mar. 27, 2014

(65) Prior Publication Data
US 2015/0239807 A1      Aug. 27, 2015

Related U.S. Application Data (60) Provisional application No. 61/703,367, filed on Sep. 20, 2012.

(51) Int. Cl.
C07C 17/013    (2006.01)
C07C 17/10     (2006.01)
C07C 17/25     (2006.01)
C07C 17/04     (2006.01)
C07C 17/38     (2006.01)

(52) U.S. Cl.
CPC .............. *C07C 17/013* (2013.01); *C07C 17/04* (2013.01); *C07C 17/10* (2013.01); *C07C 17/25* (2013.01); *C07C 17/38* (2013.01)

(58) Field of Classification Search
CPC ...... C07C 17/013; C07C 17/38; C07C 17/04; C07C 17/10; C07C 17/25
See application file for complete search history.

(56) References Cited

U.S. PATENT DOCUMENTS

| | | |
|---|---|---|
| 2,119,484 A | 5/1938 | Levine et al. |
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |
| 3,954,410 A | 5/1976 | Pohl et al. |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |

(Continued)

FOREIGN PATENT DOCUMENTS

| | | |
|---|---|---|
| CH | 609022 | 6/1974 |
| CN | 101215220 | 7/2008 |

(Continued)

OTHER PUBLICATIONS

Bai, et al., "Isomerization of Tetrachloropropene to Promote Utilization Ratio of Triallate Raw Materials", Petrochemical Technology & Application, 2007, 25(1).

Chai, et al., "Study of Preparation of 1,1,1,3-tetrachloropropane", Zhejiang Chemical Industry, 2010, pp. 1-3, 41(5).

Cristiano, et al., "Tetraalkylphosphonium Trihalides. Room Temperature Ionic Liquids as Halogenation Reagents", J. Org. Chem., 2009, pp. 9027-9033, 74.

Evstigneev, et al., "Initiated Chlorination of Tetrachloropropane", Khim. Prom., 1984, pp. 393-394, 16(7).

(Continued)

*Primary Examiner* — Shailendra Kumar (57) ABSTRACT

Processes for the production of chlorinated propenes are provided. The present processes make use of 1,2-dichloropropane, a by-product in the production of chlorohydrin, as a low cost starting material, alone or in combination with 1,2,3-trichloropropane. At least one chlorination step is conducted in the gas phase. The present processes can also generate anhydrous HCl as a byproduct that can be removed from the process and used as a feedstock for other processes, providing further time and cost savings.

19 Claims, 2 Drawing Sheets

(56) References Cited

U.S. PATENT DOCUMENTS

| | | |
|---|---|---|
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Mueller et al. |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo et al. |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0087039 A1 | 7/2002 | Tung et al. |
| 2002/0110711 A1 | 8/2002 | Boneberg et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0197842 A1 | 8/2007 | Tung |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowidjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101754941 | 6/2010 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |

(56) References Cited

FOREIGN PATENT DOCUMENTS

| | | |
|---|---|---|
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54079207 | 6/1979 |
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2008063314 | 3/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, , pp. 41-42, 39(5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.I. The Peroxide-Catalyzed Chlorination of Hydrocarbons", JACS, 1939, pp. 2142-2150, 61.

Khusnutdinov, et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Cholorination of Chloroolefins C3—C4", 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by Cp/Ru(PPh3)(PR3)Cl Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

Ochi, et al., "Preparation of Chloropropenes by Photochemical Dehydrochlorination of 1,2-Dichloropropane", Chemical Abstracts, Jul. 17, 1989, p. 574, 111(3).

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, Wi-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

(56) References Cited

OTHER PUBLICATIONS

Tanuma, et al., "Partially Fluorinated Metal Oxide Catalysts for a Friedel-Crafts-type Reaction of Dichlorofluoromethane with Tetrafluoroethylene", Catal. Lett., 2010, pp. 77-82, 136.

Tobey, et al., "Pentachlorocyclopropane", Journal of the American Chemical Society, Jun. 1, 1996, pp. 2478-2481, 88(11).

Urry, et al., "Free Radical Reactions of Diazomethane with Reactive Bromopolychloroalkane", JACS, May 5, 1964, pp. 1815-1819, 86(9.

Wang Chin-Hsien, "Elimination Reactions of polyhalopropanes under emulsion catalytic conditions to give Halopropenes", Synthesis, Jan. 1, 1982, pp. 494-496, 1982(6).

Zhao, et al., "Research Progress on Preparation Technology of 1,1,2,3-Tetrachloropropene", Zhejiang Chemical Industry, 2010, pp. 8-10, 41(6).

Zheng, et al., "Preparation of the low GWP alternative 1,3,3,3-tetrafluoropropene", Zhejiang Huagong, 2010, pp. 5-7, 41(3).

Michigan Technological Univ., "Free-Radical Chlorination with Sulfuryl Chloride", Nov. 15, 2001, 1-7.

PROCESS FOR THE PRODUCTION OF CHLORINATED PROPENES

This application is a 371 of PCT/US2013/059603, filed on Sep. 13, 2013, which claims benefit of 61/703,367, filed on Sep. 20, 2012.

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the complicated, multi-step processes typically utilized in their manufacture. This may be due at least in part to the fact that conventional processes for their manufacture may require the use of starting materials that are prohibitively expensive to be economically produced by manufacturers on the large scale required to be useful as feedstocks. Additionally, conventional processes may require multiple chlorination and dehydrochlorination steps to arrive at a desired level of chlorination in the final product. Dehydrochlorination steps are typically conducted with an aqueous base, and result in the production of large quantites of waste water containing large quantities of sodium chloride and/or chlorinated organics. Treatment of this waste water is time consuming and expensive, and results in the recovery of low value by-products.

It would thus be desirable to provide improved processes for the large capacity and/or continuous production of chlorocarbon precursors useful as feedstocks in the synthesis of refrigerants and other commercial products. More particularly, such processes would provide an improvement over the current state of the art if they were less costly in starting materials, processing time, utility costs and/or capital costs required to implement and maintain the process. Generation of byproducts having a higher value than sodium chloride, or really any value, would be a further advantage if provided in such a process.

BRIEF DESCRIPTION

The present invention provides efficient processes for the production of chlorinated propenes. Advantageously, the processes make use of 1,2-dichloropropane, a by-product in the production of chlorohydrin, as a low cost starting material, alone or in combination with 1,2,3-trichloropropane. At least one chlorination step is conducted in the gas phase, and in some embodiments, may be conducted at an elevated temperature, e.g., greater than 150° C. Performing one or more chlorinations in the gas phase can increase the efficiency of the process, since gas phase chlorinations can proceed much more quickly than liquid phase chlorinations. Because 1,2-dichloropropane, either alone or in combination with 1,2,3-trichloropropane, is directly chlorinated to chlorinated propene isomers, fewer steps are required than conventional processes, and capital cost and time savings are provided. In some embodiments, lesser amounts of chlorinated propane intermediates are processed through caustic cracking than conventional processes, and so, anhydrous HCl can be recovered from the process rather than the lower value NaCl produced by multiple caustic cracking steps. Less waste water is thus generated, providing further time and cost savings.

In one aspect, the present invention provides a process for the production of chlorinated propenes from one or more chlorinated alkanes. The process comprises at least one gas phase chlorination step. The gas phase chlorination may be carried out at an elevated temperature, e.g., greater than 150° C. The one or more chlorinated alkanes comprise 1,2-dichloropropane, and may further comprise 1,2,3-trichloropropane. Catalyst are not required for the gas-phase chlorination, but can be used, if desired. If desired, free radical initiators are suitable, including carbon tetrachloride, ethylene, propylene, allyl chloride, ultraviolet light or combinations of these. The chlorination agent for the gas-phase chlorination step comprises chlorine. HCl is generated by the process as a by-product, and in some embodiments, may be recovered in its anhydrous form for use, e.g., in downstream processes. Further, one or more reactants may be generated within or upstream of the process.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "PDC" may be used as an abbreviation for 1,2-dichloropropane, "TCP" may be used as an abbreviation for 1,2,3-trichloropropane and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the production of chlorinated propenes. The present processes comprise conducting at least one chlorination step in the gas phase on one or more chlorinated propanes comprising PDC. The use of PDC, a byproduct in many chlorohydrin processes, as a starting material is economically more attractive than disposing of it via incineration, as may be done in connection with some conventional chlorohydrin processes.

The use of at least one gas phase chlorination provides greater efficiency to the process since the reaction proceeds at a much quicker rate than liquid phase chlorinations. And, the use of lower temperatures than conventionally utilized for gas phase chlorinations not only provides utility cost savings, but also, can tend to result in lower fouling rates than those seen when higher temperatures are used. Higher fouling rates, in turn, tend to limit reactor lifetime and can lead to undesirable byproduct formation. Any other chlorinations used in the course of the process may be conducted in either the gas or liquid phase.

The gas phase chlorination may be conducted at elevated temperatures, e.g., of at least higher than 150° C., with accommodations made via the length of the reactor or processing time to provide an adequate reaction time. In some embodiments, the gas phase chlorination may desirably be conducted at elevated temperatures, e.g. of 150° C., or 175 C, or 200 C.°, or 225° C., or 250° C., or 275° C. or even 300° C. or greater. If elevated temperatures are used, the temperature should be elevated enough to see an improvement in process yield and/or selectivity, rather than a decline in the same, as may result from e.g., reactant or product decomposition. At temperatures greater than, e.g., 450° C., for example, significant decomposition of dichloropropane or its products, and/or the formation of undesirable amounts of by products, may be expected to occur, and so, in some embodiments, if the reaction occurs at an elevated temperature, the temperature will desirably not exceed 450° C., or 425° C., or 400° C.

In some embodiments, the gas phase chlorination may desirably occur at temperatures between 150° C. and 450° C. or between 175° C. and 450° C. or between 200° C. and 450° C., or between 225° C. and 450° C. or between 250° C. and 450° C. or between 275° C. and 450° C. In other embodiments, the gas phase chlorination may occur at temperatures between 150° C. and 425° C. or between 175° C. and 425° C. or between 200° C. and 425° C., or between 225° C. and 425° C. or between 250° C. and 425° C. or between 275° C. and 425° C. In yet other embodiments, the gas phase chlorination may desirably occur at temperatures between 150° C. and 400° C. or between 175° C. and 400° C. or between 200° C. and 400° C., or between 225° C. and 400° C. or between 250° C. and 400° C. or between 275° C. and 400° C.

The present processes, in some embodiments, may also provide a reduction of caustic cracking steps as compared to conventional processes, and so, anhydrous HCl can be recovered. Anhydrous HCl is of greater value than the sodium chloride that would be produced as byproduct(s) if conventional caustic cracking steps were utilized. The present process thus results in the production of a by-product that may either be sold or used as a feedstock for other processes, e.g., ethylene oxyhalogenation to produce ethylene dichloride.

The present process can make use of one or more chlorinated alkanes to produce the desired chlorinated propenes. Desirably, the one or more chlorinated alkanes comprise 1,2-dichloropropane, which may be available at low cost due to its production as a by-product in many chlorohydrin processes. The process feedstock may also comprise trichloropropane, or other chlorinated alkanes, if desired. And, the one or more chlorinated alkanes may be generated within or upstream of the process, if desired, e.g., as a byproduct in a chlorohydrin process, or by any other methods known to those of ordinary skill in the art.

Any chlorinated propene may be produced using the present method, although those with 3-5 chlorine atoms are more commercially sought after, and production of the same may thus be preferred in some embodiments. In some embodiments, the process may be used in the production of 1,1,2,3-tetrachloropropene, which is highly sought after as a feedstock for refrigerants, polymers, biocides, etc.

The gas phase chlorination may advantageously be conducted without the use of catalysts, however, catalysts can be used if desired, to enhance the present process. Free radical initiators are suitable for use, and those of ordinary skill in the art are aware of many. Exemplary free radical catalysts suitable for use in the gas phase chlorination typically include one or more chlorine atoms, and exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, the chlorinated propene(s), within the design limitations of the reactor.

Furthermore, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Surprisingly, the utilization of the same does not result in an increase in the production of impurities by the process, but does provide selectivities to the chlorinated propenes of at least 50%, or up to 60%, up to 70%, and in some embodiments, up to 80% or even higher.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4), 333-48 and Sheppard, C. S.; Mageli, O. L. "Peroxides and peroxy compounds, organic," Kirk-Othmer Encycl. Chem. Technol., 3rd Ed. (1982), 17, 27-90.

Taking the above into consideration, examples of suitable catalysts/initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, etc. Monochloropropenes, dichloropropenes, trichloropropanes and tetrachloropropanes, such as allyl chloride, ethylene and propylene, may also exhibit activity in chlorinating PDC under the conditions of this invention. Combinations of any of these may also be utilized.

The process or reactor zone may be subjected to pulse laser or continuous UV/visible light sources at a wavelength suitable for inducing photolysis of the free radical catalyst/initiator, as taught by Breslow, R. in *Organic Reaction Mechanisms* W. A. Benjamin Pub, New York p 223-224. Wavelengths from 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the reactor chamber. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

Additional chlorinations, if any, conducted within the process may be conducted in either the gas or liquid phase. For example, any chlorinations of di- or tri-chlorinated propanes or propenes may advantageously be conducted in the liquid phase, as higher yields may be seen than if these reactions are conducted in the gas phase.

If one or more chlorinations are conducted in the liquid phase, catalysts, including any of the aforementioned free radical initiators may be utilized. Additional free radical initiators may be utilized in connection with liquid phase chlorinations, and examples of these include organic and inorganic hypochlorites, including hypochlorous acid, and t-butylhypochlorite, methylhypochlorite, chlorinated amines (chloramine) and chlorinated amides or sulfonamides such as chloroamine-T®, and the like. Free radical initiators comprising one or more peroxide groups may also be used, and examples of these include hydrogen peroxide, hypochlorous acid, aliphatic and aromatic peroxides or hydroperoxides, including di-t-butyl peroxide, benzoyl peroxide, cumyl peroxide and the like. In addition, compounds, such as azobisisobutyronitrile (AIBN), 1,1'-azobis(cyclohexanecarbonitrile (ABCN), 2,2'-azobis(2,4-dimethyl valeronitrile, dimethyl 2,2'-azobis(2-methylpropionate), or 1,1'-azobis(cyclohexane-1-carbonitrile).

Or, any liquid phase chlorinations included in the process may be conducted in the presence of ionic chlorination catalysts. Ionic chlorination catalysts dehydrochlorinate and chlorinate alkanes at the same time. That is, ionic chlorination catalysts remove a chlorine and hydrogen from adjacent carbon atoms to form a double bond, and HCl is released. A chlorine is then added back, replacing the double bond, to provide a more highly chlorinated alkane.

Ionic chlorination catalysts are well known to those of ordinary skill in the art, and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof.

In some embodiments, the dehydrochlorination steps of the present process may be carried out in the presence of a catalyst so that the reaction rate is enhanced and also use of liquid caustic is reduced, or even eliminated, from the process. Such embodiments are further advantageous in that anhydrous HCl is produced, which is a higher value byproduct than aqueous HCl. If the use of catalysts is desired, suitable dehydrochlorination catalysts include, but are not limited to, aluminum chloride (AlCl3), ferric chloride ($FeCl_3$), or combinations of these, and may be used as a substitute to caustic.

In other embodiments, the dehydrochlorination steps of the present process may be conducted in the presence of a liquid caustic. Although vapor phase dehydrochlorinations advantageously result in the formation of a higher value byproduct than liquid phase dehydrochlorinations, liquid phase dehydrochlorination reactions can provide cost savings since evaporation of reactants is not required. The lower reaction temperatures used in liquid phase reactions may also result in lower fouling rates than the higher temperatures used in connection with gas phase reactions, and so reactor lifetimes may also be optimized when at least one liquid phase dehydrochlorination is utilized.

Many chemical bases are known in the art to be useful for this purpose, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts can also be added to improve the dehydrochlorination reaction rate with these chemical bases.

Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any free radical chlorination and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected that useful concentrations of the free radical initiator or ionic chlorination catalyst will range from 0.001% to 20% by weight, or from 0.01% to 10%, or from 0.1% to 5 wt. %. If a dehydrochlorination catalyst is utilized for one or more dehydrochlorination steps, useful concentrations may range from 0.01 wt. % to 5 wt. %, or from 0.05 wt. % to 2 wt. % at temperatures of 70° C. to 200° C. If a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween. Relative concentrations of each catalyst/base are given relative to the feed, e.g. 1,2-dichloropropane alone or in combination with 1,2,3-trichloropropane.

The gas-phase chlorination step is most efficiently conducted with $Cl_2$. The subsequent chlorination steps of the process may be carried out in liquid phase using any chlorination agent, and several of these are known in the art. For example, suitable liquid phase chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, mechanical mixing, etc.

That being said, the particular conditions employed at each step described herein are not critical, and are readily determined by those of ordinary skill in the art. What is important is that PDC is utilized as a starting material, and at least one chlorination occurs in the gas phase. The order of the following reaction steps is unimportant, and those of ordinary skill in the art will readily be able to determine suitable equipment for each step, as well as the particular conditions at which the chlorination, dehydrochlorination, separation, drying, and isomerization steps may be conducted.

In the present process, a feedstream comprising PDC, either alone, or in some embodiments, in combination with other alkanes such as 1,2,3-trichloropropane, is converted to TCPE using at least one gas phase chlorination step conducted either with or without the presence of a free radical catalyst/initiator.

In one exemplary embodiment, PDC is fed to a gas phase chlorination reactor, which may typically be a jet-stirred reactor, e.g., such as that described in U.S. Pat. No. 5,268,518. Such a reactor will typically operate adiabatically, and will comprise a cylindrical tube reactor having an inner diameter larger than the feed inlet inner diameter to create a back mixed zone near the reactor entrance. The molar ratio of the feed, i.e., either PDC alone or in combination with trichloropropane, to chlorine, as well as the reactor temperature, are controlled to achieve the desired maximum exit temperature and conversion.

Suitable reaction conditions include, e.g., a temperature of less than 400° C., or less than 350° C., and a pressure of from atmospheric to 1000 kPa. Desirably, PDC conversion is controlled so that the production of hexachloropropanes and 1,1,2,3,3-pentachloropropane production is minimized. As shown in Tables 1 and 2, greater than 90% conversion of PDC chlorination in the gas-phase below 400° C. to the desired products and intermediates can be achieved under the appropriate operating condition. The mono, di, and trichloropropene and tri-, tetra-, and pentachlorinated propane intermediates can be further processed to produce TCPE as described below.

The process may be carried out neat, i.e., in the absence of diluent, or, one or more diluents may be provided to the gas phase chlorination reactor, and may be provided as feedstock, or, recycled from one or more separation columns operably disposed to receive streams from the chlorination reactor. For example, tri- and tetrachloropropane intermediates may be recycled from a separation column and/or the chlorination reactor may be provided with a feedstock of any appropriate solvent for chlorination reactions, such as, e.g., carbon tetrachloride, HCl, or a combination of these.

The product stream from the chlorination reactor is cooled, and partially condensed in a quench chamber. The vapor from the quench chamber, comprising HCl, is then provided to a first separation column. This column is operated at conditions effective to provide anhydrous HCl to an overhead line thereof and chlorine through a bottom recycle line.

More particularly, the top temperature of such a column can typically be set below 0° C. or more preferably, can be set at a temperature of from −70° C. to −10° C. The bottom temperature of this column is desirably set at from 10° C. to 150° C., or from 30° C. to 100° C., with the exact temperature dependent to some degree on the bottom mixture composition. The pressure of this column is desirably set above 200 kPa or preferably, from 500 kPA to 2000 kPa, or more preferably from 500 kPa to 1000 kPa. The bottom stream of a column operated at such conditions would be expected to contain excess chlorine, unreacted PDC and monochloropropene intermediates, while the overhead stream would be expected to comprise anhydrous HCl.

The liquid from the quench chamber may be fed to a second separation column operated at conditions effective to separate the product from the bottom stream comprising the TCPE and intermediates with boiling point above 145° C. (such as 1,2,3-trichloropropane, tetra- and pentachloropropanes). The overhead stream from this separation column, comprising lighter intermediates such as mono-, di-, and trichloropropenes and unreacted PDC, tri- and tetra-chlorinated propanes, may be provided to a liquid phase chlorination reactor to convert the mono-, di-, and tri-chloropropenes to tri-, tetra-, and penta-chloropropanes, respectively. The product of this liquid phase chlorination reactor is provided to a separation column to remove PDC and trichloropropanes intermediate in the overhead stream. This overhead stream is then recycled back to the gas-phase chlorination reactor, or to a liquid phase chlorination reactor for further conversion/chlorination, while the bottom stream, expected to comprise tetrachloropropanes, pentachloropropanes and heavier by-products, such as isomers of hexachloropropanes, may be provided to a further separation column.

This fourth separation column separates TCPE, tetrachloropropanes, 1,2,3-trichloropropane, the desirable pentachloropropanes, i.e., 1,1,2,2,3-pentachloropropane, 1,1,1,2,3-pentachloropropane, and 1,1,1,2,2-pentachloropropane, from the less desirable 1,1,2,3,3-pentachloropropane and heavier components, which are purged as a bottom stream.

The overhead stream comprising 1,2,3-trichloropropane, TCPE, tetrachloropropanes, 1,1,2,2,3-pentachloropropane, 1,1,1,2,3-pentachloropropane, and 1,1,1,2,2-pentachloropropane is then provided to a reactor where it is dehydrochlorinated to provide dichloropropenes, trichloropropenes, 2,3,3,3-tetrachloropropene, and 1,1,2,3-tetrachloropropene. More specifically, dehydrochlorination reactor may typically be a batch or a continuous stirred tank reactor. The mixing can be done, e.g., by mechanical or jet mixing of feed streams. Those of ordinary skill in the art are readily able to determine the appropriate conditions at which to run a dehydrochlorination reactor in order to conduct the aforementioned dehydrochlorination.

The reaction stream from the dehydrochlorination reactor may optionally be provided to a drying column, and the dried stream therefrom provided to a further separation unit to remove di- and trichloropropenes in the overhead stream from tetrachloropropene in the bottom stream. The trichloropropene intermediate can then be recycled to a liquid phase chlorination reactor whereas the bottom stream comprising tetrachloropropenes can be fed to a reactor to isomerize the 2,3,3,3-tetrachloropropene to 1,1,2,3-tetrachloropropene under the appropriate conditions. For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite, quartz, (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758.

Figure 1:
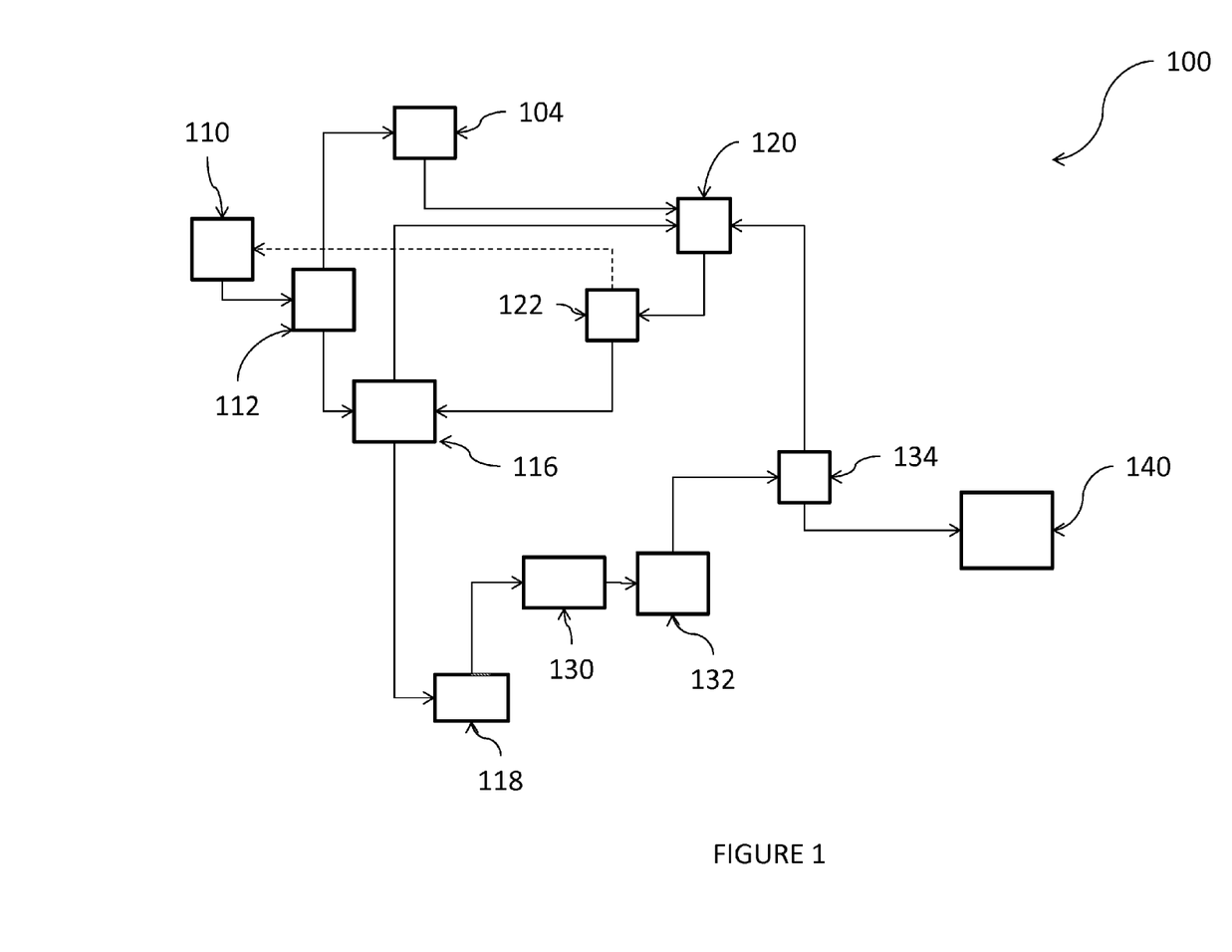
FIG. 1 shows a schematic representation of a process according to one embodiment.

A schematic illustration of such a process is shown in FIG. 1. As shown in FIG. 1, process 100 would make use of gas-phase chlorination reactor 110, liquid phase chlorination reactor 120, separation columns 104, 116, 118, 122, and 134, dehydrochlorination reactor 130, dryer 132, quench chamber 112, and isomerization reactor 140. In operation, 1,2-dichloropropane (alone or in combination with trichloropropanes) chlorine, and optionally one or more free radical catalysts such as carbon tetrachloride, allyl chloride, propylene and/or ethylene, are fed, or otherwise provided, to gas-phase chlorination reactor 110, which may be operated at any set of conditions operable to provide for the gas phase chlorination of PDC to tri-, tetra- and pentachlorinated propanes, and mono-, di-, tri-, and tetrachlorinated propenes. In some embodiments, chlorination reactor 110 may be operated at conditions effective to provide a selectivity to hexachloropropanes and 1,1,2,3,3-pentachloropropane of less than 5%, as described above, e.g., chlorination reactor may be operated at an elevated temperature, e.g., greater than ambient, or greater than 150° C.

The effluent of reactor 110 is cooled and partially condensed in quench chamber 112. The vapor stream from quench chamber 112 is fed to separation column 104, which may desirably be a distillation column. Separation column 104 is operated at conditions effective to provide anhydrous HCl through an overhead line and bottom stream comprising chlorine, PDC and monochloropropene intermediates to liquid-phase chlorination reactor 120.

The liquid stream from quench chamber 112 is fed to separation column 116, which is operated at conditions effective to separate mono-, di-, trichlorinated propenes, unreacted PDC and the trichlorinated propanes in the overhead stream from a bottom stream comprising the tetrachloropropene and heavier intermediates including 1,2,3-trichloropropane, tetrachlorinated propanes and the pentachlorinated propanes. The bottom stream of separation column 116 contains 1,2,3-trichloropropane since its relative volatility is higher than 1,1,1,2-tetrachloropropane, which has the lowest boiling points among other tetrachloropropane isomers. (see C. L. Yaws, "Thermophysical Properties of Chemicals and Hydrocarbons," 2008)

The overhead stream of unit 116 is fed to liquid phase chlorination reactor 120 where the mono-, di-, and tri-chlorinated propene intermediates are converted to tri-, tetra-, and pentachloropropane intermediates. The reaction product from chlorination reactor 120 is fed to separation column 122 to recover unreacted PDC the trichloropropane intermediate in the overhead stream, which is fed back to gas-phase chlorination reactor 110. The bottom stream from separation column 122 comprising mostly tetra- and pentachloropropanes is fed back to separation column 116.

The bottom stream of separation column 116 is fed to separation column 118, which separates it into an overhead stream comprising the 1,2,3-trichloropropane, product TCPE, tetrachloropropanes, desirable pentachloropropane isomers (1,1,1,2,2-pentachloropropane, 1,1,2,2,3-pentachloropropane and 1,1,1,2,3-pentachloropropane) and a bottom stream comprising the less desirable 1,1,2,3,3-pentachloropropane, hexachloropropane and heavier by-products. The overhead stream is fed to dehydrochlorination reactor 130, while the bottoms stream is appropriately disposed of [not shown].

Within dehydrochlorination reactor 130, the desirable pentachloropropane isomers are dehydrochlorinated, or cracked, using sodium hydroxide to provide 2,3,3,3-tetrachloroprene and 1,1,2,3-tetrachloropropene, while the tetrachloropropanes and 1,2,3-trichloropropane are converted to di- and trichloropropenes. The conditions to do the dehydrochlorination reactions are either well-known, or readily determined, by those of ordinary skill in the art. Generally speaking, dehydrochlorination reactor 130 may be charged with caustic soda at 50% aqueous solution at concentration of from 0.01 grmole/L to 100 grmole/L, or from 0.1 grmole/L to 10 grmole/L, and operated at pressures of from ambient to 400 kPA and temperature of from 40° C. to 150° C., or from 60° C. to 120° C. and at residence times of less than 3 hours.

The product stream of dehydrochlorination reactor 130 is fed to drying unit 132, and then to a separation column 134. Separation column 134 is operated at conditions effective to provide di- and trichloropropene intermediates as an overhead stream and TCPE its isomer, 2,3,3,3-tetrachloropropene as a bottom stream. The overhead stream is provided to liquid phase chlorination reactor 120 for further chlorination. The bottom stream is further provided to the isomerization reactor 140, wherein the dried 2,3,3,3-tetrachloropropene is isomerized to TCPE using catalyst as described in, e.g., U.S. Pat. No. 3,926,758.

Figure 2:
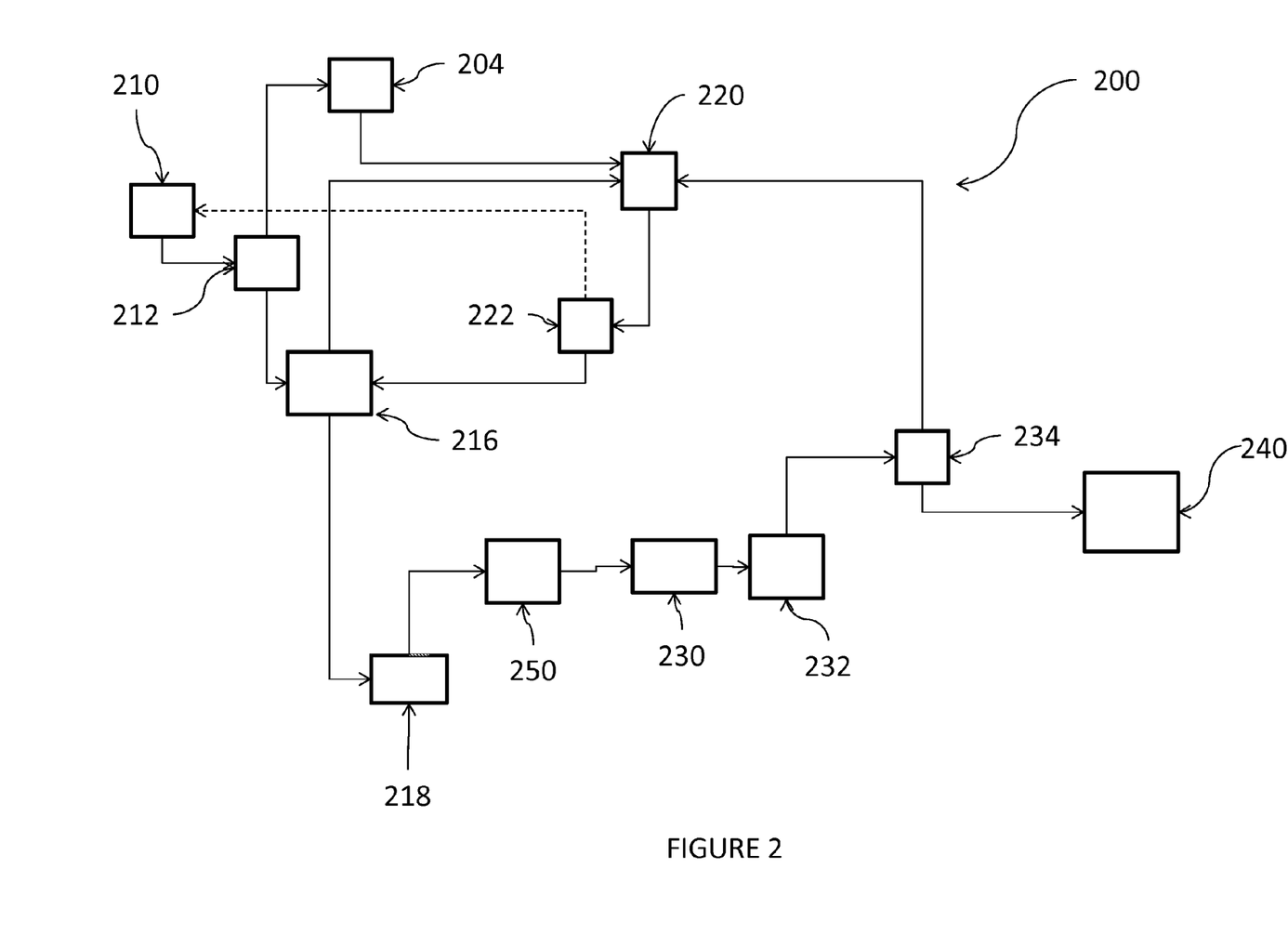
FIG. 2 shows a schematic representation of a process according to a further embodiment.

A schematic illustration of another embodiment of the process is shown in FIG. 2. As shown in FIG. 2, process 200 could operate on equipment comprising gas phase chlorination reactor 210 and liquid phase chlorination reactor 222, separation columns 204, 216, 218, 222, and 234, dehydrochlorination reactors 230 and 250, dryer 232, quench chamber 212, and isomerization reactor 240. The process as shown in FIG. 2 thus makes use of one additional dehydrochlorination reactor 250, yet operates in much the same way.

In operation, 1,2-dichloropropane (alone or in combination with trichloropropane) and the desired chlorination agent (e.g., chlorine), and optionally, one or more free radical initiators such as carbon tetrachloride, allyl chloride, are fed to chlorination reactor 210, which may be operated at any set of conditions operable to provide for the chlorination of PDC to tri-, tetra and pentachlorinated propanes and mono-, di-, tri-, and tetrachloropropenes.

The process 200 is operated in the same way as that in process 100, except that an the overhead stream of separation unit 218 comprising 1,2,3-trichloropropane, tetrachloropropane, TCPE, and pentachloropropane is first provided to a dehydrochlorination reactor 250 where some of the tetrachloropropanes and pentachloropropane isomers are catalytically dehydrochlorinated to trichloropropene and tetrachloropropene, e.g., using $FeCl_3$, $AlCl_3$, or a combination of these. Anhydrous HCl byproduct from reactor 250 is removed and fed to unit 204 for further purification. The product stream from dehydrochlorination reactor 250 is fed to caustic dehydrochlorination reactor 230, where the unreacted tri-, tetra- and pentachloropropane(s) are caustic cracked to provide di-, tri-, and tetrachloropropene(s). The overall product is processed as described in process 100.

The chlorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated propenes to provide hydrofluoroolefins may broadly comprise a single reaction or two or more reactions involving fluorination of a compound of the formula $C(X)_m CCl(Y)_n (C)(X)_m$ to at least one compound of the formula $CF_3 CF=CHZ$, where each X, Y and Z is independently H, F, Cl, I or Br, and each m is independently 1, 2 or 3 and n is 0 or 1. A more specific example might involve a multi-step process wherein a feedstock of a chlorinated is fluorinated in a catalyzed, gas phase reaction to form a compound such as 1-chloro-3,3,3-trifluoropropene (1233zd). The 1-chloro-2,3,3,3-tetrafluoropropane is then dehydrochlorinated to 1,3,3,3-tetrafluoropropene via a catalyzed, gas phase reaction.

In the following examples, individual chloropropane isomers are identified by reference to the positions of the chlorine atoms, i.e., 112 indicates 1,1,2-trichloropropane, 1123 indicates 1,1,2,3-tetrachloropropane, 11223 indicates 1,1,2,2,3-pentachloropropane, and so on. For chlorinated propenes, similar nomenclature is used, with an "e" added as a suffix, e.g., 112e indicates 1,1,2-trichloropropene, 1123e indicates 1,1,2,3-tetrachloropropene, 11223e indicates 1,1,2,2,3-pentachloropropene, and so on.

Example I

PDC (1,2-dichloropropane) is preheated and mixed with chlorine gas at a molar ratio of 0.5 $PDC/Cl_2$ and a temperature of from 300° C. to 400° C. in a ¼ inch ID preheated reactor tube at a pressure of 22 psig. After a residence time of from 4.2 to 4.6 seconds, the product is quenched. The expected product composition is shown in Table I. As shown, although the concentration of the desired intermediates declines at temperatures of 350° C. and higher, the concentration of the less desired intermediates remains low in comparison.

TABLE I

| res. Time(s) | 4.59 | 4.22 | 4.59 |
|---|---|---|---|
| Temperature (° C.) | 300 | 350 | 400 |
| % chlorine conversion | 63.42 | 95.33 | 100 |
| organic product (mole %) | | | |
| Total % desired intermediates | 93.79 | 68.45 | 63.51 |

TABLE I-continued

| 112 | 29.56 | 10.39 | 9.74 |
|---|---|---|---|
| 122 | 16.43 | 4.11 | 1.32 |
| cis13e | 16.27 | 11.60 | 11.89 |
| 1223 | 6.61 | 2.20 | 0.56 |
| t13e | 6.43 | 4.83 | 5.30 |
| 123 | 4.69 | 0.03 | 0.01 |
| 113e | 3.44 | 10.01 | 10.25 |
| 23e | 3.42 | 9.51 | 14.45 |
| t123e | 2.07 | 6.22 | 3.68 |
| cis123e | 1.62 | 4.81 | 2.83 |
| TCPE | 1.36 | 3.69 | 2.92 |
| 1123 | 1.35 | 0.56 | 0.21 |
| 233e | 0.53 | 0.50 | 0.36 |
| Less desired intermediates | | | |
| 11233 | 1.84 | 5.61 | 2.70 |
| 1133e | 0.33 | 1.22 | 1.77 |
| Trans133e | 0.18 | 0.37 | 0.47 |
| Cis133e | 0.15 | 0.32 | 0.42 |
| Ethanes | 1.36 | 10.41 | 16.49 |
| methanes | 0.97 | 10.48 | 14.56 |

Example II

In this example, Example 1 is repeated, except the reactor is maintained at a temperature of 300° C. and a pressure of 21.5 psig to determine the impact of $PDC/Cl_2$ ratio on the formation of desired intermediates. The resulting product composition is shown in Table II.

As shown, decreasing the $PDC/Cl_2$ ratio increases PDC conversion and the production of higher chlorinated C3 intermediates. This example thus shows that a $PDC/Cl_2$ ratio between 0.5 and 4 can maximize the conversion of both PDC and $Cl_2$ while maintaining selectivity to the desired intermediates above 90%.

TABLE II

| $PDC/Cl_2$ molar | 7.87 | 3.99 | 2.01 | 1.01 | 0.50 |
|---|---|---|---|---|---|
| res. Time(s) | 3.64 | 3.28 | 2.74 | 2.06 | 2.29 |
| % PDC conversion | 68.06 | 82.55 | 95.91 | 99.00 | 99.98 |
| % C12 conversion | 100.00 | 100.00 | 100.00 | 78.58 | 53.46 |
| Organic product (mole %) | | | | | |
| % desired intermediates | 99.92 | 99.87 | 99.54 | 98.44 | 93.92 |
| 2e | 25.87 | 23.45 | 18.42 | 12.02 | 4.10 |
| 3e | 19.42 | 14.30 | 7.17 | 1.19 | 0.02 |
| cis1e | 18.87 | 18.00 | 13.99 | 6.84 | 0.84 |
| trans1e | 17.24 | 14.11 | 9.52 | 4.39 | 0.50 |
| 123 | 8.31 | 12.24 | 16.18 | 18.92 | 12.84 |
| 112 | 2.90 | 5.61 | 11.32 | 22.45 | 31.26 |
| cis13e | 2.20 | 3.67 | 7.31 | 9.50 | 13.10 |
| 23e | 1.94 | 2.98 | 5.38 | 5.85 | 4.58 |
| 122 | 1.78 | 3.23 | 5.94 | 11.10 | 16.81 |
| trans13 | 1.21 | 1.94 | 3.55 | 4.34 | 5.44 |
| 33e | 0.07 | 0.09 | 0.09 | 0.07 | 0.04 |
| 113e | 0.05 | 0.13 | 0.41 | 0.93 | 1.90 |
| 11e | 0.04 | 0.07 | 0.09 | 0.18 | 0.13 |
| 233e | 0.01 | 0.04 | 0.12 | 0.29 | 0.51 |
| 1123 | | | 0.02 | 0.19 | 0.82 |
| TCPE | | | 0.01 | 0.09 | 0.49 |
| Trans123e | | | 0.02 | 0.09 | 0.52 |
| 1223 | | | 0.15 | 0.94 | 4.09 |
| Less desired intermediates | | | | | |
| 11233 | | | 0.02 | 0.11 | 0.52 |
| Trans133e | | | 0.07 | 0.09 | 0.13 |
| Cis133e | | | 0.06 | 0.07 | 0.11 |
| Ethanes | | | | 0.05 | 0.19 |
| methanes | | | | 0.06 | 0.23 |

The invention claimed is:

1. A process for the production of chlorinated propanes and/or propenes from one or more chlorinated alkanes comprising 1,2-dichloropropane, comprising at least one gas phase chlorination step conducted at a pressure greater than ambient, a temperature less than 400° C., and under reaction conditions sufficient to achieve at least 90% conversion of the 1,2-dichloropropane.

2. The process of claim 1, wherein the gas phase chlorination reaction is conducted at a temperature of between 150° C. and 400° C.

3. The process of claim 1, wherein the gas phase chlorination is conducted at a temperature of between 250° C. and 350° C.

4. The process of claim 1, wherein the gas phase chlorination reaction is conducted in the presence of a free radical initiator.

5. The process of claim 1, wherein the gas phase chlorination reaction is the first reaction step.

6. The process of claim 1, wherein the one or more chlorinated alkanes further comprise 1,2,3-trichloropropane.

7. The process of claim 1, wherein the chlorination agent for the gas phase chlorination step comprises chlorine.

8. The process of claim 7, wherein the ratio of 1,2-dichloropropane to chlorine is from 0.5 to 4.

9. The process of claim 4, wherein the free radical initiator comprises carbon tetrachloride, allyl chloride, propylene, UV light, or combinations of these.

10. The process of claim 1, wherein the chlorinated propene comprises 2 to 4 chlorine atoms.

11. The process of claim 1, wherein HCl and/or chlorine are generated as byproduct(s).

12. The process of claim 11, wherein the chlorine is recovered and recycled to a chlorination step.

13. The process of claim 1, wherein the at least one gas phase chlorination step generates a product stream comprising di, tri, and tetrachloropropenes, tri-, tetra- and pentachloropropanes and unreacted 1,2-dichloropropane.

14. The process of claim 13, wherein the product stream is further purified to remove 11233-pentachloropropane and heavier byproducts.

15. The process of claim 13, wherein the di- and trichloropropenes are purified and provided to a second chlorination step to provide tetra- and pentachlorinated propanes.

16. The process of claim 1, comprising at least one liquid phase chlorination.

17. The process of claim 16, wherein the at least one liquid phase chlorination is carried out in the presence of a free radical initiator or ionic chlorination catalyst.

18. The process of claim 17, wherein the free radical initiator comprises hypochlorous acid, hydrogen peroxide, di-t-butyl peroxide, benzoyl peroxide, azobisisobutyronitrile (AIBN), 1,1'-azobis(cyclohexanecarbonitrile) (ABCN), 2,2'-azobis(2,4-dimethyl valeronitrile, dimethyl 2,2'-azobis(2-methylpropionate), 1,1'-azobis(cyclohexane-I-carbonitrile) or a combination of these.

19. The process of claim 17, wherein the ionic chlorination catalyst comprises aluminum chloride, ferric chloride ($FeCl_3$) and other iron containing compounds, iodine, sulfur, antimony pentachloride ($SbCl_5$), boron trichloride ($BCl_3$), one or more lanthanum halides, one or more metal triflates, or a combination of these.

* * * * *